United States Patent [19]
Wells et al.

[11] Patent Number: 5,580,541
[45] Date of Patent: Dec. 3, 1996

[54] METHOD OF CONVEYING LIQUID MATERIALS AND DEVICE FOR THE AUTOMATED ELUTION OF A RADIONUCLIDIC GENERATOR

[75] Inventors: Charles P. Wells, Canterbury; Andrew G. Kettle, Margate, both of England

[73] Assignee: Mallinkrodt Medical, Inc., St. Louis, Mo.

[21] Appl. No.: 129,189

[22] PCT Filed: Apr. 30, 1992

[86] PCT No.: PCT/US92/03564

§ 371 Date: Oct. 6, 1993

§ 102(e) Date: Oct. 6, 1993

[87] PCT Pub. No.: WO92/20071

PCT Pub. Date: Nov. 12, 1992

[30] Foreign Application Priority Data

May 1, 1991 [EP] European Pat. Off. ............... 91201036

[51] Int. Cl.$^6$ ................................................ A61K 51/00
[52] U.S. Cl. ..................... 424/1.11; 250/435; 422/63; 422/100; 422/159
[58] Field of Search ................ 137/93, 205; 250/430, 250/431, 432, 435, 45; 252/301.1 R, 631; 422/62, 63, 100, 159; 423/249, 2; 424/1.11

[56] References Cited

U.S. PATENT DOCUMENTS

| | | | |
|---|---|---|---|
| 2,732,502 | 1/1956 | Darney | 250/45 |
| 3,774,036 | 11/1973 | Gerhart | 252/301.1 R |
| 3,898,044 | 8/1975 | Strecker et al. | 23/252 R |
| 3,901,656 | 8/1975 | Durkos et al. | 23/230 B |
| 4,280,053 | 7/1981 | Evans et al. | 250/432 PD |
| 4,625,118 | 11/1986 | Kriwetz et al. | 250/432 PD |
| 4,746,490 | 5/1988 | Sanell | 422/62 |
| 4,782,231 | 11/1988 | Svoboda et al. | 250/432 PD |

Primary Examiner—Charles T. Jordan
Assistant Examiner—John R. Hardet
Attorney, Agent, or Firm—Thomas P. McBride

[57] ABSTRACT

The invention relates to a method of conveying liquid materials in closed systems without mutual contamination, comprising flushing the conduit with an inert gas between introduction of the materials into said conduit and using a peristaltic pump for introducing said materials, in which after each flushing operation for a moment said pump is made to rotate in the reverse direction.

The invention further relates to a method for the automated elution of a radionuclide generator and delivery of a radiopharmaceutical liquid, in particular a Tc99m-pertechnetate solution, whereas said above method is used, and to a device for performing said method for elution and delivery of a radiopharmaceutical liquid.

6 Claims, 1 Drawing Sheet

METHOD OF CONVEYING LIQUID MATERIALS AND DEVICE FOR THE AUTOMATED ELUTION OF A RADIONUCLIDIC GENERATOR

The invention relates to a method of conveying liquid materials in closed systems without mutual contamination.

Especially in hospitals and clinics often hazardous liquid materials are handled. Preferably such materials are kept in closed systems as much as possible to diminish the risk of contamination of the environment, including the attendant personnel, with such materials. It is always difficult to avoid contamination of such liquid materials with other liquid materials, e.g. rinsing fluids, or, vice versa, of these rinsing fluids with such hazardous liquid materials in closed systems. In the former case undesired dilution of the hazardous liquid material, e.g. a pharmaceutical liquid, takes place, in the latter case the rinsing fluid is no longer environmentally unsuspected. Conventionally the system is flushed with an inert gas, e.g. nitrogen, to remove the first liquid material as far as possible before introducing the second liquid material.

More in particular the present invention relates to a method as mentioned in the opening paragraph, comprising the steps of (i) introducing a first liquid material into a main conduit through a first inflow conduit provided with a first valve, (ii) closing said first valve and flushing said main conduit with an inert gas, (iti) stopping the flushing operation and introducing a second material into said main conduit through a second inflow conduit provided with a second valve, (iv) closing said second valve and repeating said flushing operation, and (v), optionally after introducing in a corresponding manner a third liquid material through a third inflow conduit with valve, repeating the above operations. It has been observed, however, that after the flushing operation an aliquot of the liquid material, just introduced into the main conduit, is still present between the valve and the connection between inflow conduit and main conduit, said aliquot with its convex outer surface projecting into the main conduit. Part of this aliquot is entrained by the other liquid material, next introduced into the main conduit, and consequently contaminates this latter liquid material.

According to the present invention it has now been found, that this problem can be avoided by using a peristaltic pump for the introduction of the liquid materials into the main conduit and by making said pump to rotate for a moment in the reverse direction after each flushing operation. By taking the above measures, mutual contamination of the liquid materials can be avoided completely. Peristaltic pumps are to be understood to comprise tube pumps.

It will be clear from the above, that the method of the invention is intended in particular for conveying liquid materials, one of which is a pharmaceutical liquid, especially a radiopharmaceutical liquid. A radiopharmaceutical liquid is notoriously hazardous for the environment. In general the other liquid will be a rinsing liquid, intended for removing the radioactivity from the closed system, i.e. the main conduit, as completely as possible.

The above method according to the present invention is pre-eminently suitable for use in an automated system for elution and delivery of radiopharmaceutical liquids. Consequently, the present invention also relates to a method for the automated elution of a radionuclide generator and delivery of a radiopharmaceutical liquid, in particular a Tc99m-pertechnetate solution, in a generator-eluting and delivery device, comprising a mutually connected solvent reservoir, radionuclide generator, pump means, eluate reservoir and delivery station, said method comprising the steps of (a) rinsing of the interconnecting means by flushing said means with a solvent, (b) program-controlled elution of said generator with a predetermined quantity of said solvent and transfer of the resulting eluate to said eluate reservoir, the radioactivity of the eluate in the reservoir being continuously monitored, (c) program-controlled discharge of a predetermined quantity of the eluate and, if desired, simultaneously a predetermined quantity of said solvent for diluting purposes into said delivery station, from which a controlled quantity of a radiopharmaceutical liquid can be dispensed into a vial. Such a generator-eluting and delivery device is described in the European patent specification 0141800 and, in particular for dispensing a Tc99m-pertechnetate solution, in a publication by Fueger et al in Nucl. Med. Comm. 8, 1987, 733–749. This device, marketed under the trade name Elumark(R), is particularly intended for dispensing Tc99m-pertechnetate in a vial comprising a substance to be radiolabelled with Tc99m. Examples of such substances are certain phosphonates, colloids, complex-forming ligands, peptides and biological macro-molecules such as proteins.

It has been observed, however, that by employing the above-described device for the labelling of certain substances as defined above, serious labelling problems occur, as are expressed in low and/or fluctuating labelling yields. Surprisingly it has been found, that the presence of even small traces of disinfecting or sterilizing substances which are used in disinfecting the eluate reservoir, the tubings and the pump of the above device at the beginning and the end of the daily routine, can dramatically influence the labelling yield. Examples of such substances which are usually employed for disinfecting purposes are alcohols, in particular propanol, aqueous hydrogen peroxide solution and aqueous sodium hypochlorite solution.

The influence of the presence of traces of propanol on the elution yield and consequently on the labelling yield is convincingly demonstrated in Applicant's copending and non-prepublished European patent application 91200555.0. The influence of sodium hypochlorite on the labelling yield is demonstrated by the following experiments. Kits are labelled with Tc99m in an automated generator-eluting and delivery device as described above, wherein the tubing has been disinfected by using 5% w/v sodium hypochlorite solution, compared to normal saline flushing. The labelling yields are determined, using ITLC. The following results are obtained:

| preparation | labelling yield | |
|---|---|---|
| | normal | NaOCl |
| Tc99m-MAG3 | 97.2 | 45.6 |
| Tc99m-HMDP | 98.7 | 44.8 |
| Tc99m-DTPA | 99.3 | 99.3 |
| Tc99m-DMSA | 100.0 | 100.0 |
| Tc99m-HSA | 96.9 | 96.4 |

The above kit preparations comprise as the substances to be labelled: mercaptoacetylglycylglycylglycine (MAG3), hydroxymathylene diphosphonate (HMDP), diethylenatriamine pentaacatic acid (IYrPA), dimarcaptosuccinic acid (DMSA) and human serum albumin (HSA). As will be apparent from the above results, the disinfection with a NaOCl-solution has a disastrous effect on the labelling of two kit preparations, viz Tc99m-MAG3 and Tc99m-HMDP; apparently the other kit preparations, which are not affected by the disinfectant, are less sensitive. There exists also a serious risk, what traces of the disinfectant are present in the kit preparation after the labelling procedure and then will be injected into the patient.

The above-described known device has a further disadvantage in that it can be used for the labelling of more than one kit preparation only after various manipulations. As a matter of fact, after the dispensing procedure the labelline vial should be detached from the delivery station and a next vial should be attached. Between detachman end attachment the risk of air oxygen contamination of the interior of the device and of compromising the sterility is not excluded.

It is therefore a further object of the present invention to provide a method for the automated elution of a radionuclide generator and delivery of a radiopharmaceutical liquid, in particular a Tc99m-pertechnetate solution, in a generator-eluting and delivery device, as described hereinbefore, wherein the above disadvantages do not occur.

This object can be achieved by a method, comprising the steps of (a) rinsing of the interconnecting means by flushing said means with a solvent, (b) program-controlled elution of said generator with a predetermined quantity of said solvent and transfer of the resulting eluate to said eluate reservoir, the radioactivity of the eluate in the reservoir being continuously monitored, (c) program-controlled discharge of a predetermined quantity of the eluate and, if desired, simultaneously a predetermined quantity of said solvent for diluting purposes into said delivery station, from which a controlled quantity of a radiopharmaceutical liquid can be dispensed into a vial, said method being characterized according to the present invention in that:

a peristaltic pump is used as said pump means;

an inert gas supply is connected to the device;

between steps (a) and (b) and between steps (b) and (c) the interconnecting means are flushed with inert gas and subsequently for a moment said pump is made to rotate in the reverse direction, as claimed in claim 1; and step (c) is repeated, preceded by a flushing operation and following reverse pumping operation.

By using a peristaltic pump and an inert gas supply any mutual contamination of fluids conveyed in the device, e.g. eluate and solvent or eluent (generally saline solution), can be avoided. As described hereinbefore, a short rotation of the pump in the reverse direction following the inert gas flush eliminates any such mutual contamination. The system, using an integrated inert gas supply, allows the dispensing of the radiopharmaceutical liquid into a great number of vials without intermediate detachment and attachment of the vials, so without any manipulations. The repetition of this dispensing step, viz. the above step (c), is, of course, program-controlled, warranting an accurate radioactivity and quantity of the delivered and dispensed radiopharmaceutical liquid. The computer program allows an individual selection of radioactivity and quantity for each separate vial.

The use of a peristaltic pump, viz. a tube pump, in a device for eluting a radionuclide generator is known from U.S. Pat. No. 3,898,044. The device described in this patent, however, is not intended for the automated elution and delivery. In addition, said publication does not mention or suggest the favourable use of such a pump together with inert gas flushing in order to avoid mutual contamination of fluids in the device.

The invention also relates to a device for performing the method as defined above, comprising in addition to a program-control unit: a solvent reservoir, a radionuclide generator, a pump means, an eluate reservoir externally provided with a radioactivity-monitoring facility, and a delivery station, in a mutually connected condition constituted by a disposable tubing provided with valves. According to the present invention, this device is characterized in that:

said pump means is a tube pump, an inert gas supply is additionally connected to the device, and the disposable tubing is provided with tube-clamping valves.

The use of a tube pump, disposable tubing and tube-clamping valves, e.g. pressure valves, in the device of the invention, is particularly favourable in that is often the opportunity to replace the pump tubes and the disposable tubing as a single unit together with the generator. This still better guarantees the sterility of the system, because the liquids conveyed in the device are only in contact with the interior of the sterilized tubings. This as opposed to the device described above and marketed as Elumark$^{(R)}$, wherein a fluid-contact pump is used, viz. a Hamilton dilutor, and wherein fluid-contact valves are used. The used clamping valves require an accurate choice of the tubing material and wall thickness, as well as an exactly adjusted clamping stroke, to avoid any sticking or distortion of the tubes at the clamping area during use of the device.

In said Elumark$^{(R)}$ device the radioactivity of the eluate is monitored by using a semi-conductor. Such a semi-conductor, however, should be recalibrated from time to time due to aging effects. Further in this known device the quantity of the eluate in the eluate reservoir is measured by its volume.

As an extra aspect of the present invention, it has been found, that recalibration of the detector can be avoided by using an ionization chamber instead of a semi-conductor. In addition, an ionization chamber can be situated around the eluate reservoir and therefore allows a particularly accurate measuring of the radioactivity of the contents thereof. In addition, if desired, the eluate reservoir may be positioned on a balance to measure the quantity of eluate in said reservoir by weighing. Weighing is a more accurate method of determining the quantity of a certain liquid than measuring the volume, as in the known device.

Preferably the device of the present invention is provided with a controlled inflow facility to maintain a slight overpressure of inert gas in the device. A slight overpressure is favourable to avoid any environmental contamination of the interior of the device.

In a pre-eminently favourable embodiment the device of the present invention is constructed in such a way, that the delivery station comprises a plurality of program-controlled, sequentially opened exit ports, each of which is connectible to a vial. This facility, avoiding any risk of the simultaneous opening of more than one exit port, is included in the computer program.

DETAILED DESCRIPTION OF THE INVENTION

Figure 1:
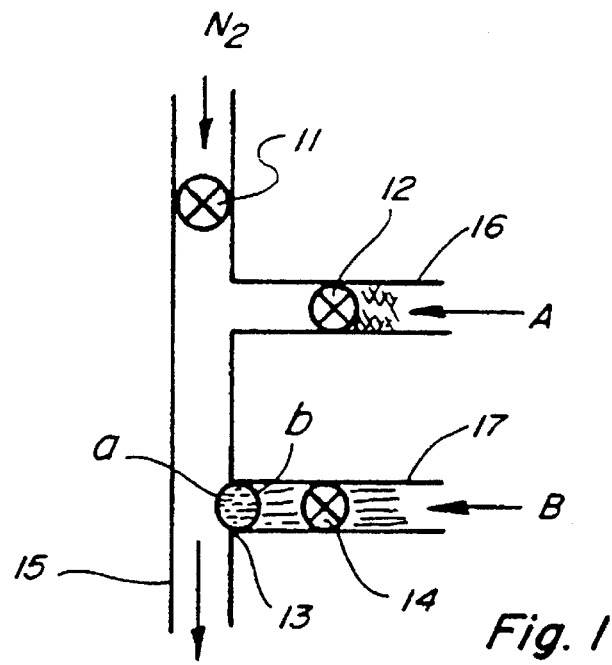
FIG. 1 represents a detailed view of the tubing of the device of the present invention.
Figure 2:
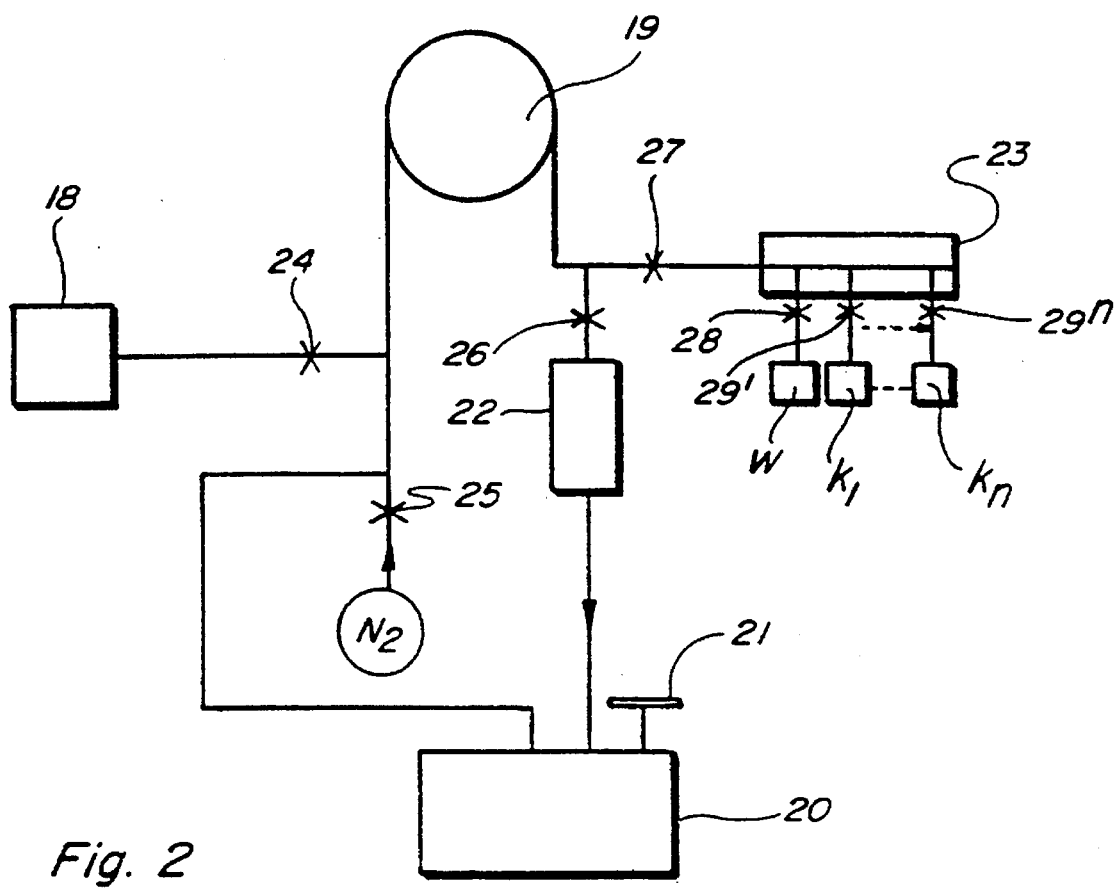
FIG. 2 represents a schematic of the device of the present invention.

The invention will now be described in greater detail with reference to the drawings, in which FIG. 2 is a simplified scheme, showing the most relevant functional parts of a device for elution and delivery of a Tc99m-pertechnetate solution, according to the invention, and in which FIG. 1 shows in more detail a part of the tubing of the same device.

The tubing portion shown in FIG. 1 comprises a main conduit 15, to which two inflow conduits 16 and 17, respectively, both provided with valves (12 and 14, respectively), are connected. The main conduit is also provided with a valve 11 and is connected to a nitrogen source. Inflow conduit 16 is fed by one fluid, e.g. a radiopharmaceutical liquid such as a Tc99m-pertechnetate solution, in the direction of arrow A.

Inflow conduit 17 is fed by another fluid, e.g. a rinsing fluid such as a saline solution, in the direction of arrow B. After opening of valve for example, said saline solution can be pumped in the direction of the arrows into the main conduit. Fluid supply is stopped by closing valve 14. After opening valve 11 nitrogen can be flushed through the main conduit to remove the saline solution therefrom. After nitrogen flush an aliquot of said saline solution remains present between the connection 13, between main conduit and inflow conduit 17, and the valve 14, said aliquot projecting with its convex outer surface (position "a") into the main conduit. When the tube pump (not shown in FIG. 1) is made to rotate in the reverse direction (valve 11 opened), the outer surface of this aliquot of liquid changes to position "b". Now the valve 11 is closed, valve 12 is opened and the Tc99m-pertechnetate solution can be pumped in the direction of the arrows into the main conduit. Entraining of an aliquot of the saline solution by the pertechnetate solution is completely avoided and the fluid is not contaminated.

The simplified scheme shown in FIG. 2 comprises in addition to an $N_2$ source ($N_2$): a solvent or eluent reservoir 18 with a saline solution, a tube pump 19, an eluate reservoir 20, externally provided with a radioactivity-monitoring facility in the form of an ionization chamber and positioned on a balance (both not shown in the caps figure), an air valve 21 with a bacterial filter, a Mo99-Tc99m generator 22, and a delivery station 23, to which a waste bottle w and kit vials $k_1 \ldots k_n$ are connected. The various parts of the device are mutually connected by disposable tubing provided with tube-clamping or pressure valves: 24, 25, 26, 27, 28 and $29^1 \ldots 29^n$.

Upon use, saline solution is pumped from reservoir 18 through the system into the waste bottle (valves 24, 27 and 28 open). Then $N_2$ flush (valves 25 and 28 open), followed by reverse rotation of pump (see above). Thereupon the generator is eluted by pumping saline solution through the generator into the eluate reservoir 20 (valves 24 and 26 open). Again $N_2$ flush and reversed rotation of pump. Then a predetermined quantity of the eluate (valves 27 and $29^1$ open), if desired together with a predetermined quantity of saline solution (valve 24 also open), is pumped into the delivery station and is directly dispensed in kit vial $k_1$. After $N_2$ flush and reversed rotation of pump this discharge-dispense operation can be repeated with sequentially opened valves $29^2 \ldots 29^n$, depleting into kit vials $k_2 \ldots k_n$. It will be obvious from the description hereinbefore, that the quantities and radioactivities of the supplied liquids are continuously monitored and that all conveying operations are program-controlled.

We claim:

1. A method of conveying different liquid materials, including a first liquid material and a second liquid material, in a closed system without mutual contamination, comprising the steps of (i) introducing the first liquid material into a main conduit through a first inflow conduit-provided with a first valve for conveyance through the main conduit in a conveying direction, (ii) closing said first valve and flushing said main conduit in the conveying direction with an inert gas, (iii) stopping the flushing operation and introducing a second liquid material into said main conduit through a second inflow conduit provided with a second valve for conveyance through the main conduit in a conveying direction, and (iv) closing said second valve and repeating said flushing operation, characterized in that the main conduit comprises flexible disposable tubing, that the steps of introducing the first liquid material and of introducing the second liquid material into the main conduit are effected with the aid of a peristaltic pump disposed downstream in the conveying direction from the first valve and from the second valve and acting in the conveying direction on flexible disposable tubing of the main conduit, that the first inflow conduit and the second inflow conduit each comprise flexible disposable tubing between the respective valve and the junction of the respective inflow conduit with the main conduit, and that after each flushing operation the peristaltic pump is made to operate in a direction opposite to the conveying direction for a short period sufficient to cause the position of the surface of a potentially contaminating outer surface (a) of an aliquot of liquid in the respective inflow conduit to change to a non-contaminating position (b).

2. A method according to claim 1, characterized in that it further includes the step of (v) introducing into the main conduit a third liquid material through a third inflow conduit provided with a third valve for conveyance through the main conduit in a conveying direction, the third inflow conduit comprising flexible disposable tubing between the third valve and the junction of the third inflow conduit with the main conduit, followed by flushing of the main conduit in the conveying direction with an inert gas, and operation of the peristaltic pump for a short period in a direction opposite to the conveying direction.

3. A method according to claim 2, characterized in that two different liquid materials are conveyed, the second of which is a pharmaceutical liquid, such as a radiopharmaceutical liquid, and the first of which is a rinsing fluid.

4. A method according to claim 3 for the automated elution of a radionuclide generator and delivery of a radiopharmaceutical liquid, characterized in that the main conduit is used to convey in the conveying direction an eluent or solvent as said first liquid material from an eluent or solvent reservoir and an eluate from a radionuclide generator as said second liquid material, said eluate having been produced by passage of eluent through the radionuclide generator under program control from a program control unit and having been collected in an eluate reservoir in which the radioactivity of the eluate is continuously monitored, that said main conduit is connected to a delivery station from which a controlled quantity of a radiopharmaceutical liquid comprising the eluate from the radionuclide generator can be dispensed into a vial ($k_1 \ldots k_n$), that the method comprises (A) rinsing flexible disposable tubing of the main conduit leading to the delivery station by flushing in the conveying direction with eluent or solvent from the eluent or solvent reservoir, the first valve being closed at the end of the rinsing step, (B) elution of the radionuclide generator under program control with a program-controlled predetermined quantity of eluent from the eluent reservoir into the eluate reservoir, and (C) dispensing under program control a program-controlled predetermined quantity of the eluate from the eluate reservoir through the main conduit in the conveying direction into a vial ($k_1 \ldots k_{n-1}$) at the delivery station, the second valve being closed at the end of the dispensing step, that between steps (A) and (B) and between steps (B) and (C) the main conduit is flushed in the conveying direction with an inert gas supplied through an inert gas inlet valve and then, while the inert gas inlet valve remains open, the peristaltic pump is made to operate in a direction opposite to the conveying direction for a short period, and that step (C) is then repeated for a further vial ($k_2 \ldots k_n$).

5. A method according to claim 4, characterized in that during the dispensing step (C) a program-controlled predetermined quantity of eluent is simultaneously dispensed from the eluent reservoir to the delivery station to dilute the eluate.

6. A method according to claim 5, characterized in that the radionuclide generator delivers a Tc99m-pertechnetate solution.

* * * * *